US008813751B2

(12) United States Patent
Filho

(10) Patent No.: US 8,813,751 B2
(45) Date of Patent: Aug. 26, 2014

(54) PROBE FOR MEDICAL USE

(76) Inventor: Luiz Gonzaga Granja Filho, Recife (BR)

(*) Notice: Subject to any disclaimer, the term of this patent is extended or adjusted under 35 U.S.C. 154(b) by 1879 days.

(21) Appl. No.: 10/566,208

(22) PCT Filed: Jul. 28, 2003

(86) PCT No.: PCT/BR03/00109
§ 371 (c)(1),
(2), (4) Date: May 16, 2008

(87) PCT Pub. No.: WO2005/009522
PCT Pub. Date: Feb. 3, 2005

(65) Prior Publication Data
US 2008/0223374 A1    Sep. 18, 2008

(51) Int. Cl.
*A61M 16/00*    (2006.01)
(52) U.S. Cl.
USPC ............. 128/207.15; 128/207.14; 128/204.18
(58) Field of Classification Search
USPC ............. 128/204.28, 204.21–204.23, 205.23, 128/207.14–207.15
See application file for complete search history.

(56) References Cited

U.S. PATENT DOCUMENTS

| | | | | |
|---|---|---|---|---|
| 4,059,852 A | * | 11/1977 | Crane | 2/456 |
| 4,351,328 A | * | 9/1982 | Bodai | 128/202.16 |
| 4,791,923 A | | 12/1988 | Shapiro | |
| 4,825,862 A | * | 5/1989 | Sato et al. | 128/207.15 |
| 4,834,726 A | * | 5/1989 | Lambert | 604/540 |
| 4,850,349 A | * | 7/1989 | Farahany | 128/207.15 |
| 4,944,310 A | * | 7/1990 | Sullivan | 128/848 |
| 5,315,992 A | | 5/1994 | Dalton | |
| 5,452,715 A | | 9/1995 | Boussignac | |
| 5,544,648 A | * | 8/1996 | Fischer, Jr. | 128/207.14 |
| 6,254,591 B1 | * | 7/2001 | Roberson | 604/541 |
| 6,463,927 B1 | | 10/2002 | Pagan | |
| 6,513,527 B1 | * | 2/2003 | Abdel-Aziz | 128/207.14 |
| 6,651,666 B1 | * | 11/2003 | Owens | 128/207.16 |
| 2001/0013345 A1 | * | 8/2001 | Bertram | 128/200.26 |

FOREIGN PATENT DOCUMENTS

GB    2168256 A  *  6/1986  ............ A61M 16/04

* cited by examiner

*Primary Examiner* — Rachel Young
(74) *Attorney, Agent, or Firm* — Volpe and Koenig, P.C.

(57) ABSTRACT

A probe for medical use comprising a tube (1) and a cuff (3) located around the tube (1) in a region of its external wall, the cuff (3) being inflatable through a conduit (5) arranged at the wall of the tube (1), linking the interior of the tube (1) to the interior of the cuff (3), the inflation and deflation of the cuff (3) being determined by the rhythms of the inspiration and expiration of air, respectively.

13 Claims, 6 Drawing Sheets

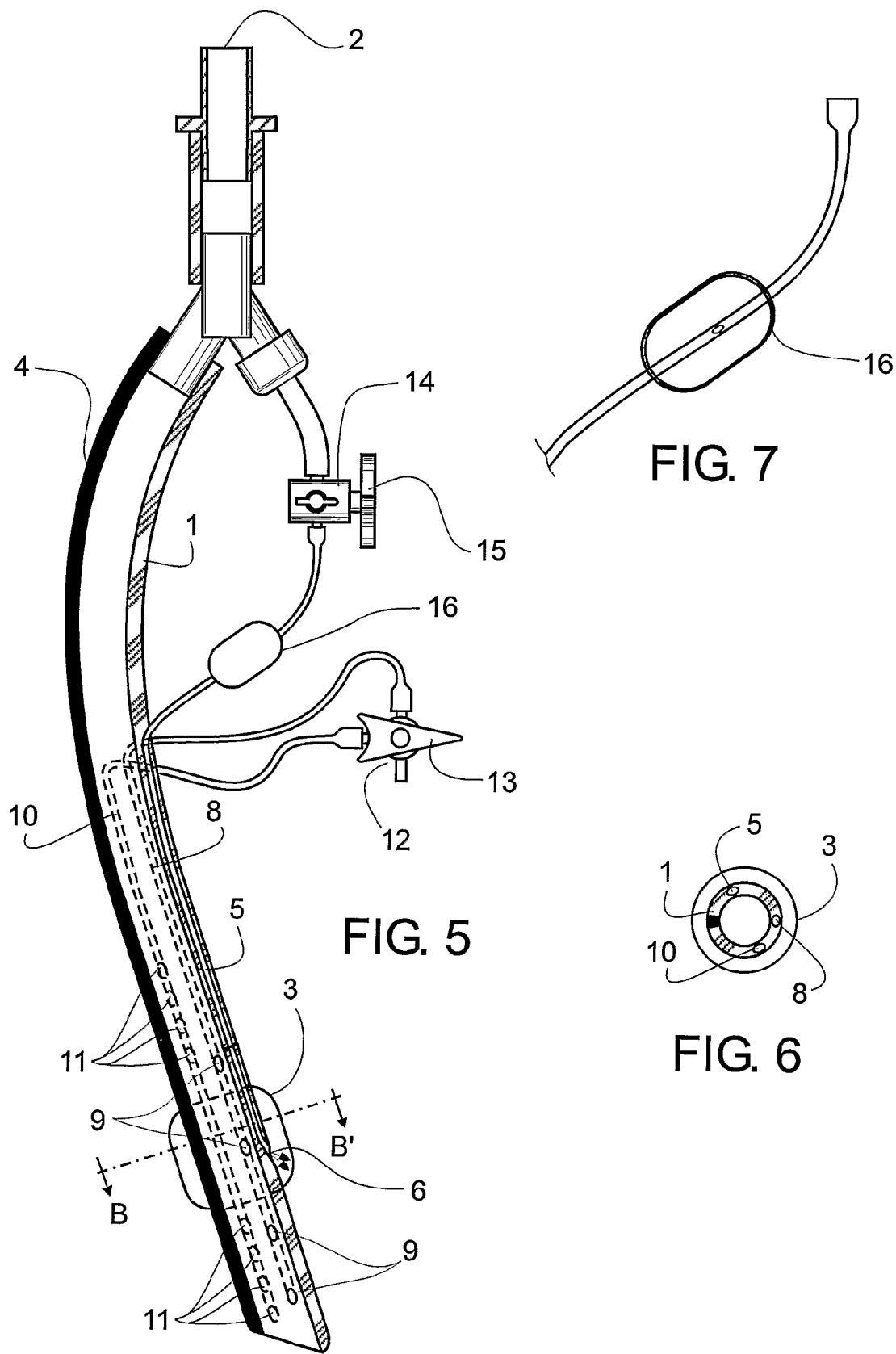

PROBE FOR MEDICAL USE

FIELD OF INVENTION

The present invention relates to a probe for intubation of patients in several medical/surgical procedures (for example, oro- and nasotracheal, tracheostomy intubation probe, etc.) of the type basically consisting of a tube through which air is supplied into a patient's body, and an inflatable cuff used for preventing extravasation of the supplied air, causing the air flow to go in and out always through the tube (and not through the region between the tube and the intubated tubular organ); for controlling the internal pressure of the airways and further for fixing the probe to the walls of a passageway of the human body, and located around part of the external wall of the tube.

DESCRIPTION OF THE PRIOR ART

Several types of probes, which are used for intubating patients, are known.

A serious drawback of the probes of the prior art is that said cuff, which accounts for fixing the probe at a determined place on the human body, remains inflated throughout the intubating period, which may cause injuries to the patients if said period is prolonged, by reason of the total or partial stoppage of blood circulation in the region where the cuff exerts pressure on the walls of the passageway of the human body where the intubation is made, for example, the trachea of a patient. Moreover, in some cases, the cuff is inflated by inserting a fluid (usually iodine) into it by means of a syringe. This procedure is not carried out in a totally precise and safe way. Excessive inflation of the cuff is another factor that contributes to the occurrence of said mentioned injuries.

Moreover, in the case of the probes of the prior art, the conformation of the probe for introduction into the human body is carried out with the help of a metallic thread, inserted into the probe tube. The insertion of the metallic thread into the probe tube may damage some organ or some tissue of the patient, in case the metallic thread exceeds the length of the probe tube.

U.S. Pat. No. 4,697,574 deals with a coronary and circulatory assistance pump that uses cuffs for blocking the aorta and the coronary arteries in diastole. According to that patent, the passageway for blood from the aorta is kept opened by means of a system of two cuffs that are sequentially inflated and deflated, the sequence being determined by signals from an electrocardiogram apparatus, which are used as commands for sequentially inflating and deflating the two cuffs for the purpose of never interrupting the flow of blood in the aorta, which would obviously cause the death of the patient. This solution, however, besides being specific for use in the aorta, is of technically complex construction, needing two cuffs and, chiefly, imposing an artificial rhythm of opening and closing the blood-circulation passageway, which is undesirable from the physiological point of view.

OBJECTIVES OF THE INVENTION

An objective of the present invention is to prevent injuries caused by prolonged intubation of a patient with a probe provided with an inflatable cuff.

Another objective of the present invention is to provide more tranquility to the physician in performing surgeries that require a longer time for intubating the patient.

A further objective of the present invention is to prevent possible injuries caused by inserting the metallic thread into the tube in order to conform the probe.

A further objective of the present invention is to prevent the cuff from being excessively inflated, which would cause injuries to the patient.

The above-described objectives of the invention are achieved by means of the probe that will be described in greater detail later.

SUMMARY OF THE INVENTION

The present invention has achieved the above-cited objectives by means of a probe for medical use, which basically consists of a tube designed for receiving blown air, and a first cuff arranged around the tube in a region of its external wall, said first cuff being inflatable by means of a first conduit located at the tube wall, which account for communication of the inside of the first cuff with the inside of the tube. Thus, the insufflation of the first cuff is commanded by the flow of air injected into the tube during the inspiratory movement, causing the probe to be fixed to the walls of the passageway of the human body that is being intubated; whereas the deflation of said first cuff takes place when the air is expelled from the patient's lung through the tube during the expiratory movement. This causes the first cuff to deflate temporarily, thus alleviating the mechanical pressure on the walls of said passageway of the human body and making blood circulation possible until a new flow of air is injected, which may come from an artificial breathing apparatus or from the normal breathing of the patient.

Thus, said first cuff is inflated during the inspiration and deflated during the expiration at the natural rhythm of the patient's respiration or artificial breathing apparatus. In this way the above-mentioned problems of the prior art are eliminated and the probe of the present invention has an ideal performance from the physiological point of view.

According to a preferred embodiment of the invention, the probe further comprises means that provide the tube with an elastic memory, located on the tube wall and consisting of a guide thread made from a radiopaque flexible material. Such means simultaneously allow one to mold the probe tube and to view the probe on an X-ray photograph, for instance.

According to another embodiment of the invention, the probe for medical use comprises, in addition to the tube, the first cuff and the first conduit in the tube wall that communicates the interior of the tube with the interior of the cuff, a second and a third conduits in the tube wall, which extend along the length of the tube and are couplable to an external aspiration device.

The second conduit has bores close to an end, which provide communication of the inside of the second conduit with the inside of the tube, the other end being connectable to a suction device, thus allowing the secretions existing inside the probe tube to be sucked, which prevents the tube from being clogged.

The third conduit, on its turn, has bores close to one of its ends, which provide communication of the inside of the third conduit with the external region of the tube, the other end being connectable to a suction device, so that the secretions existing inside the tube can also be sucked.

In addition, the second and third conduits are connectable by their ends to a first 3-way connection means, coupled to the external suction device and provided with a switch that permits suction at each of the conduits separately or at both conduits at the same time. In this way, depending upon the position of the switch, either the secretions existing inside the tube alone can be sucked (through the second conduit) or the secretions existing in the external region of the tube (through the third conduit), as well as the secretions of both regions at the same time.

According to an embodiment of the present invention, the first conduit is connectable to a second 3-way connection means, provided with a switch that enables one to control the operation mode of the probe. In this way, the probe may also be used in the conventional manner, with non-physiological pressure, depending upon the position of the switch. In this case, the cuff is inflated by injecting a fluid into one of the ways of the connection means and remains permanently inflated.

The probe is further provided with a second monitoring cuff, located around the first conduit, also linked to the inside of the first conduit in the region close to the opening of the tube that receives air insufflation, which is inflated and deflated at the same rhythm as the inflation and deflation of the first cuff takes place. The second cuff is used for monitoring the functioning of the first cuff, since it will only be inflated if the first cuff is intact.

Another probe embodiment is also provided, the probe having two tubes coupled side by side, one of them being longer than the other, permitting selective insulation of one lung, for example, by connecting an artificial breathing apparatus to one of the probe tubes and simultaneously inflating the first cuffs of each tube, the first cuff of the first tube being close to the bronchia, and the first cuff of the second tube being in the trachea region. For this purpose, the air outlet of the tube cuff that is not connected to the artificial breathing apparatus should be kept closed. If, on the other hand, one wishes to effect the selective inflation of the other lung, for example, one connects the artificial breathing apparatus to the other tube, closing the air outlet of the tube cuff that is not connected to said breathing apparatus.

BRIEF DESCRIPTION OF THE DRAWINGS

FIG. 5 shows a cross-section view of a fourth embodiment of a probe for medical use, which illustrates the probe tube, the first cuff, the first conduit located at the tube wall, having an opening into the interior of the first cuff and an opening into the tube, the radiopaque flexible rod, the second and third conduits, provided with bores and arranged at the tube wall, through which the secretions existing inside and outside the probe tube are sucked, the first and second connection means, as well as the second cuff for monitoring the first cuff.

FIG. 6 is a top view from the BB' section of the fourth probe embodiment illustrated in FIG. 5, which shows the first cuff, the first conduit, the second conduit and the third conduit, located at the tube wall along the length of the tube, as well as the radiopaque flexible rod.

FIG. 7 is a cross-section view showing, in detail, the second cuff, which communicates with the first conduit, which accounts for monitoring the first cuff.

DETAILED DESCRIPTION OF THE FIGURES

Figure 1:
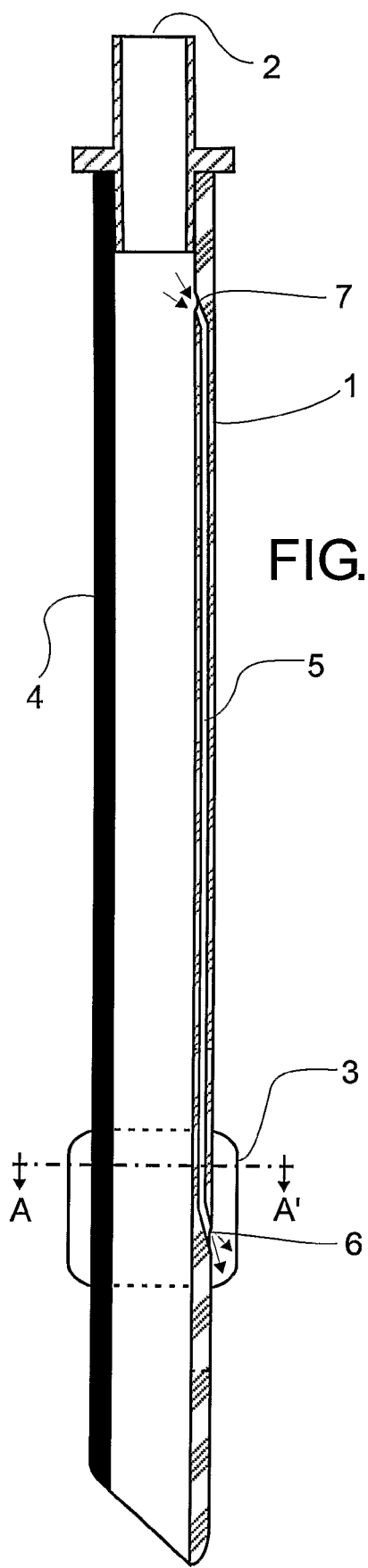
FIG. 1 shows a cross-section view of a first embodiment of the probe for medical use of the present invention, the figure illustrating the probe tube, the first cuff, the first conduit located at the tube wall, having an opening into the interior of the first cuff and an opening into the interior of the tube, as well as the means that provide the tube with an elastic memory, which consists of a radiopaque flexible rod in the preferred embodiment of the invention.

FIG. 1 illustrates a first embodiment of the probe for medical use of the present invention. This first embodiment comprises a tube 1, provided with at least one opening 2 to receive air insufflation, and a first cuff 3, arranged around the tube 1 in a region of its external wall, which is inflatable by means of a first conduit 5 arranged at the wall of the tube 1, having an opening into the interior of the first cuff 6 and another opening into the interior of the tube 7. The inflation of the first cuff 3 occurs by injecting a flow of air into the opening of the tube of the probe 2 during the inspiration, bringing about the fixation of the probe to the walls of the passageway of the human body that is being intubated. The deflation of the first cuff 3, in turn, occurs in the period of time in which air is expelled from the patient's lungs through the probe tube 1, that is, during the expiration, providing a relief of the mechanical pressure that was being exerted by the first cuff 3 on the walls of said passageway of the human body and making blood circulation possible in this region until a new flow of air is injected into the human body. Thus, the inflation and deflation of the first cuff 3 take place following the rhythm itself of the patient's respiration (inspiration and expiration, respectively), which makes the probe physiologically ideal. It should be pointed out that the flow of air insufflated into the tube 1 of the probe may also come from an artificial breathing apparatus.

In addition, FIG. 1 shows the means 4 that provide the probe tube 1 with an elastic memory, located at the tube wall along the length of the tube 1. Such means 4 consist of a guide thread made from a flexible and radiopaque material, which enables one to mold the probe tube 1 and to view the probe in an X-ray photograph and to effect tracheal intubation without the use of a laryngoscope.

Figure 2:
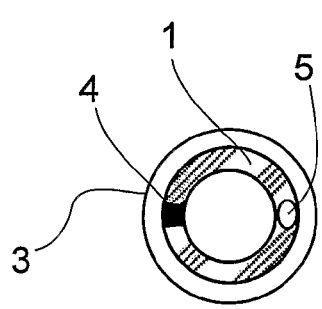
FIG. 2 is a top view from the AA' section of the first probe embodiment illustrated in FIG. 1, which shows the first cuff, the first conduit, located at the tube wall along the length of the tube, and the radiopaque flexible rod.

FIG. 2 is a top view from the section AA' of the first probe embodiment illustrated in FIG. 1. In this figure, one illustrates the first cuff 3, arranged around the tube 1, and the first conduit 5, located at the tube wall along the length of the tube, which has an opening into the interior of the first cuff 6 and a second opening into the interior of the tube 7.

Figure 3:
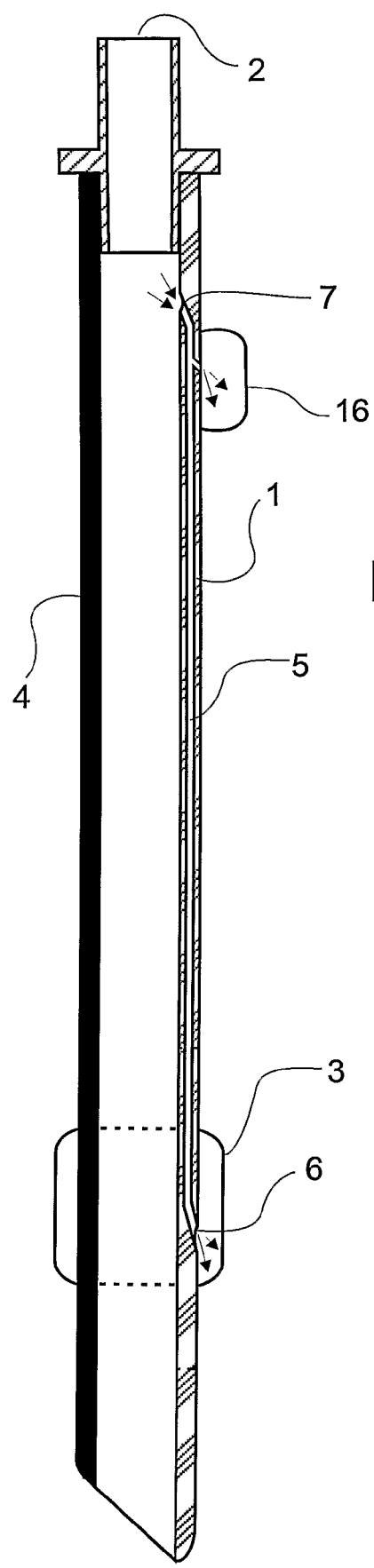
FIG. 3 shows a cross-section view of a second probe embodiment according to the present invention, the figure illustrating the probe tube, the first cuff, the first conduit located at the tube wall, having an opening into the interior of the first cuff and an opening into the interior of the tube, the radiopaque flexible rod and the second cuff, which monitors the functioning of the first cuff.

FIG. 3 illustrates a second probe embodiment for medical use, which also consists of a tube 1, which will receive air insufflation; a first cuff 3, arranged around the tube 1, in a region of its external wall, said first cuff 3 being inflatable by means of the conduit 5 arranged at the tube wall, having an opening into the interior of the first cuff 6 and another opening into the interior of the tube 7; and means 4 that provide the probe tube 1 with an elastic memory, located at the tube wall along the length of the tube 1. It should be pointed out that the inflation and deflation of the first cuff 3 are effected by following the procedure described above for the first probe embodiment for medical use.

The probe of this second embodiment, illustrated in FIG. 3, is further provided with a second cuff 16 for monitoring, which is also linked to the inside of the first conduit 5 in the region close to the opening 2 of the tube that receives air insulation and is inflated and deflated together with the first cuff 3. The second cuff 16 monitors the functioning of the first cuff 3, and is only inflated if the first cuff 3 is intact.

Figure 4:
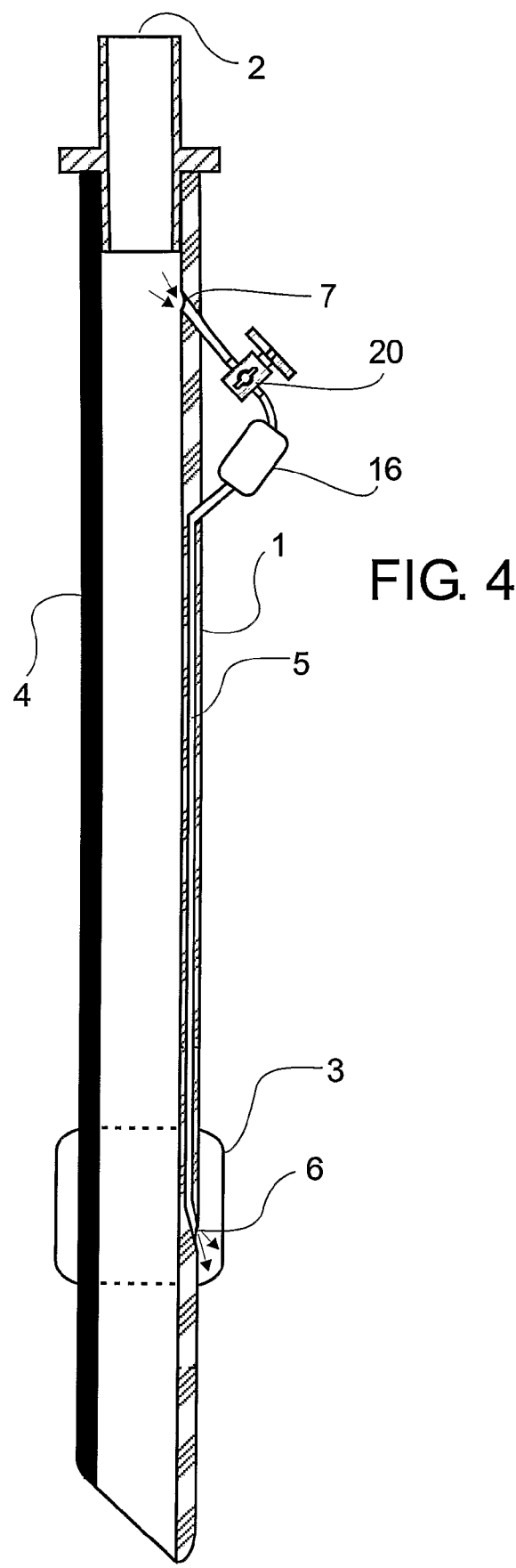
FIG. 4 is a cross-section view of a third probe embodiment of the present invention, illustrating, in addition to the components described in FIG. 3 (probe tube, first cuff, first conduit located at the tube wall with an opening into the interior of the first cuff and a second opening into the interior of the tube, radiopaque flexible rod and second cuff), the connection means, which enables the probe to be used as a conventional probe, with active inflation of the first cuff by means of a syringe, or else with passive inflation of the first cuff at the moment of inspiration with the physiological pressure of the airways, the backflow of air during expiration being immediately closed, thus maintaining the first cuff permanently inflated.

FIG. 4 illustrates a third probe embodiment for medical use, comprising the same elements of the probe embodiment of FIG. 3, described above. The inflation and deflation of the first cuff 3 is effected by the same procedure of the embodiment of the preceding figure.

In the probe embodiment of FIG. 4, the first conduit 5 is connected to a connection means 20, provided with a switch that enables one to control the probe operation mode. In this way, the probe may also be used in a conventional manner, with non-physiological pressure, the first cuff 3 being inflated, in this case, by insertion of a fluid and remaining permanently inflated or, further, with passive inflation of the first cuff 3 at the moment of inspiration, with the physiological pressure of the airways, the backflow of air and deflation of the first cuff 3 being prevented by closing the connection means 20. In this way, the first cuff 3 remains permanently inflated, but with physiological pressure of the airways.

Another embodiment of the probe for medical use is shown in FIG. 5, which also comprises a tube 1, which will receive air insulation; a first cuff 3, arranged around the tube 1 in a region of its external wall, said first cuff 3 being inflatable through a first conduit 5 arranged at the tube wall, having an opening into the interior of the first cuff 6 and another opening into the interior of the tube 7. The inflation and deflation of the first cuff 3 are effected by following the same procedure described above for the first embodiment of a probe for medical use.

FIG. 5 also shows the means 4 that provide the probe tube 1 with an elastic memory, located at the tube wall along the length of the tube 1, consisting of a guide thread made from a flexible and radiopaque material that permits the molding of the probe tube 1, the viewing probe in an X-ray photograph and the tracheal intubation without the use of a laryngoscope.

In addition, the probe embodiment shown in FIG. 5 further comprises a second conduit 8 and a third conduit 10, located at the tube wall and extending along the length of said tube 1, said second conduit 8 being provided with bores 9 close to one of its ends, linking the interior of the tube with the interior of the second conduit 8, whereas the other end is couplable to an external suction means, and the third conduit 10 being provided with bores 11 close to one of its ends, linking the interior of the third conduit 10 to the external region of the tube 1, while the other end of the third conduit 10 is couplable to an external suction means. In this way, the secretions existing inside the tube 1 and in the external region of the tube 1 may be sucked through the second 8 and the third 10 conduits, respectively, thus preventing any obstruction of the passageway for the flow of air that may be caused by the presence of such secretions. The second 8 and third 10 conduits are also connectable to a first 3-way connection means 12, provided with a switch 13 for controlling the suction of secretions through the second 8 and third 10 conduits 10, said first connection means 12 being coupled to an external suction means. Depending upon the position of the switch 13, either the secretions located inside the tube 1 alone or those located in the external region of the tube 1 alone can be sucked, or the secretions of both the regions can be sucked at the same time.

According to an embodiment of the present invention, the first conduit 5 is connectable to a second 3-way connection means 14, provided with a switch 15 that enables one to control the probe operation mode. In this way, the probe may also be used in the conventional manner, with non-physiological pressure, depending upon the position of the switch 15, the first cuff 3 being inflated, in this case, by inserting a fluid into one of the ways fo the second connection means 14, and remaining permanently inflated, or else with passive inflation of the first cuff 3 at the time of inspiration, with physiological pressure of the airways, the backflow of air and the deflation of the first cuff 3 being prevented by closing the connection means 20. In this way, the first cuff 3 remains permanently inflated, but with the physiological pressure of the airways.

The probe shown in FIG. 5 is further provided with a second cuff 16 intended for monitoring, located around the first conduit 5, also linked to the interior of the first conduit 5 in the region close to the opening 2 of the tube that receives air insufflation, which is inflated and deflated in conjunction with the first cuff 3. The second cuff 16 monitors the functioning of the first cuff 3 and is only inflated if the first cuff 3 is intact.

FIG. 6 is a top view from the section BB' of the probe embodiment illustrated in FIG. 5. This figure illustrates the first cuff 3, the first conduit 5, the second conduit 8 and the third conduit 10, arranged at the tube wall along the length of the tube.

FIG. 7 shows a second cuff 16 similar to the first one 3, which communicates with the first conduit 5 and is inflated and deflated in conjunction with the first cuff 3. The second cuff 16 is located close to the end of the tube where the opening 2 that receives air insulation is located. The second cuff 16 is inflated and deflated at the same rhythm of the inflation and deflation of the first cuff 3, being used for monitoring the first cuff 3, since its inflation will only occur if the first cuff 3 is intact.

Figure 8:
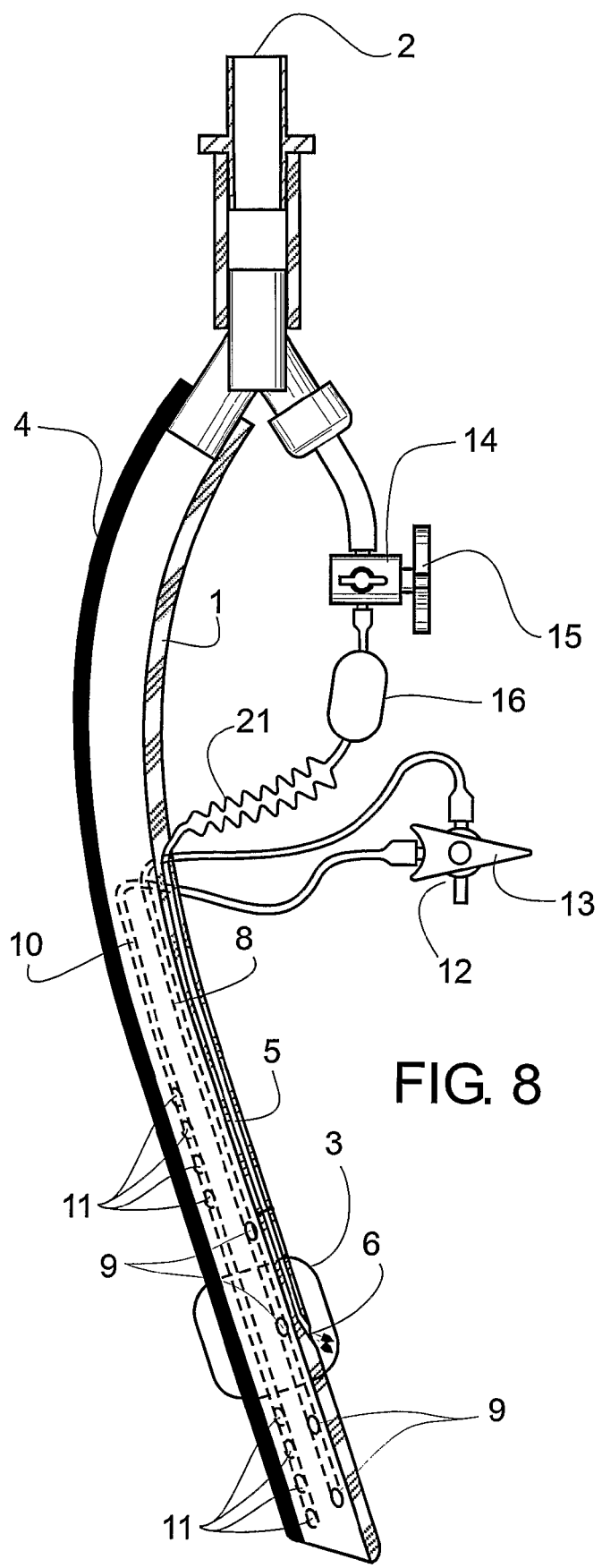
FIG. 8 is a cross-section view of a fifth embodiment of the probe of the present invention, illustrating, in addition to the components described in FIG. 5 (probe tube, first cuff, first conduit, radiopaque flexible rod, second and third conduits, first and second connection means and second cuff), the detail of a portion of the first conduit that is connected to the second cuff and which is external to the tube wall and concertina, whereby its length may be adjusted if it is necessary to cut the probe.

FIG. 8 illustrates a fifth embodiment of a probe for medical use, which comprises the same elements and has the same operation mode of the probe embodiment of FIG. 5, described above. However, in this probe embodiment, the first conduit 5 has a concertina portion 21 outside the tube wall, close to the end connected to the second cuff 16. In this way, the length of the first conduit 5 may be adjusted, if it is necessary to cut the probe in order to reduce the dead space.

Figure 9:
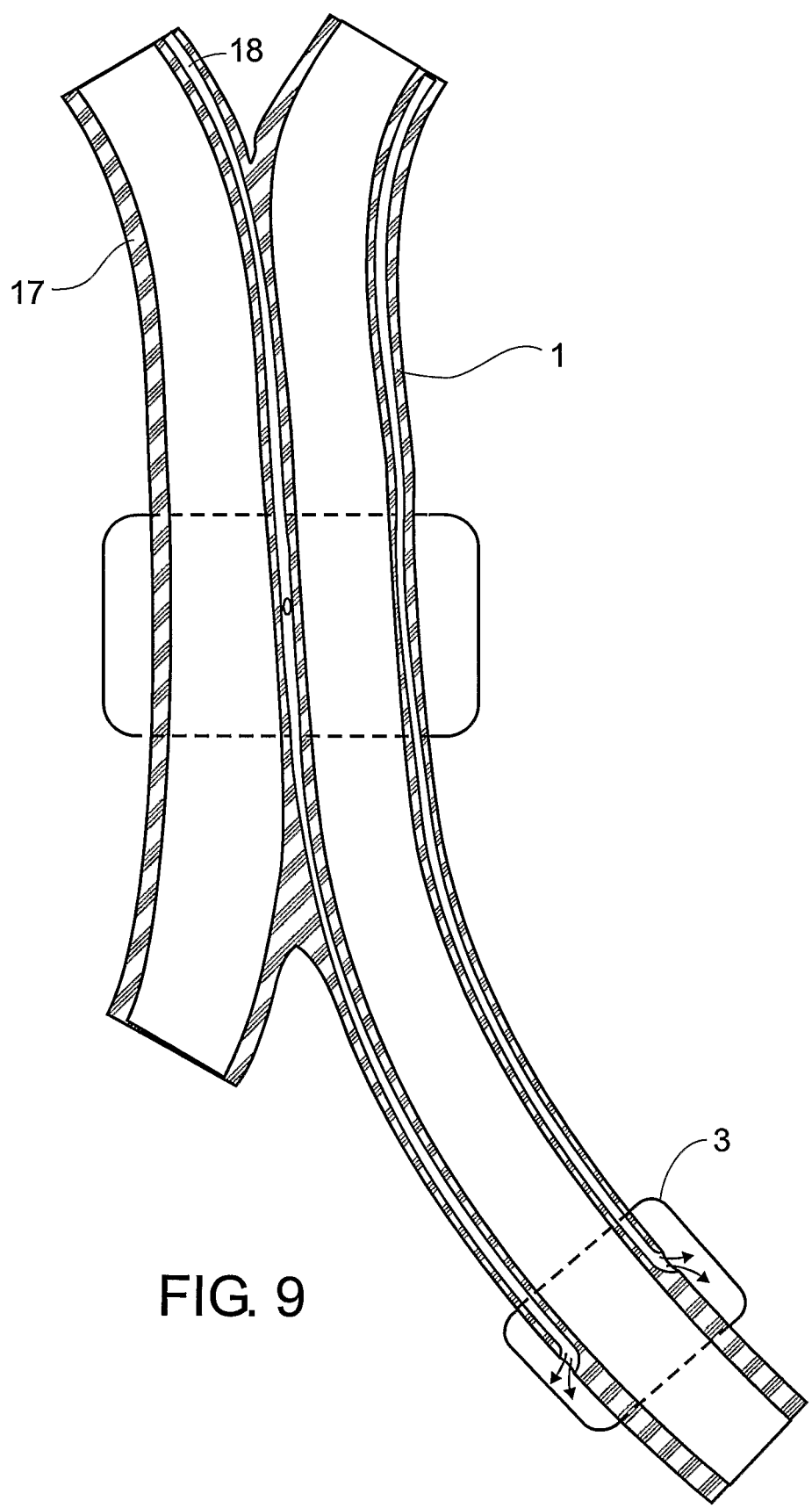
FIG. 9 shows another embodiment of the probe for medical use with the same characteristics of the above-described embodiments, but further comprising a second tube similar to the first one, laterally coupled to the first tube, having a shorter length than the latter and a first conduit that communicates the interior of the second tube with the interior of the first cuff of the second tube, said first conduit extending as far as the inside of the first cuff of the first tube.

FIG. 9 shows another embodiment of a probe for medical use with the same characteristics of the embodiments described above, but further comprising a second tube 17, similar to the first one 1, that is to say, being also provided with at least one opening for receiving air insufflation, and a first cuff arranged around the tube 17 in a region of its external wall, inflatable through a first conduit 18 arranged at the tube wall 17, having an opening into the interior of the first cuff and another opening into the interior of the tube 17, this first conduit extending as far as the inside of the first cuff 3 of the first tube 1. The inflation and deflation of the first cuff of the second tube 17 occurs in the same way described previously for the first cuff 3 of the first tube 1. This second tube 17 is laterally coupled to the first tube 1 and is shorter than the first tube 1.

It should be understood that the probe for medical use and its components described above are only a few embodiments that might exist. The real scope of the object of the invention is defined in the accompanying claims.

The invention claimed is:

1. A probe for medical use comprising:
   a first tube having at least one opening for receiving air insufflation;
   a first cuff, for the first tube arranged around the first tube in a region of its external wall; said first cuff being inflatable through a first conduit;
   a second tube having at least one opening for receiving air insufflation; said second tube being laterally coupled to the first tube;
   a first cuff for the second tube, arranged around both the first tube and the second tube in a region of their external walls, said first cuff for the second tube being inflatable through a first conduit of the second tube, wherein the first conduit of the first tube has an opening into the interior of the first cuff for the first tube and another opening into the interior of the first tube; and the first conduit of the second tube has an opening into the interior of the first cuff for the second tube and another opening into the interior of the second tube and extends into the inside of the first cuff for the first tube.

2. A probe according to claim 1, comprising a second cuff linked to the interior of the first conduit of the first tube to be inflated and deflated in conjunction with the first cuff, for the first tube located close to the end of the first tube where the opening that receives air insufflation is located.

3. A probe according to claim 2, wherein the first conduit of the first tube is a passageway made in the wall of the first tube, having a portion outside the wall of the first tube.

4. A probe according to claim 3, wherein said portion of the first conduit of the first tube outside the wall of the first tube is concertina shaped close to the end connected to the second cuff.

5. A probe according to claim 1, wherein said second tube is shorter than the first tube.

6. A probe according to claim 1, wherein the first cuff for the first tube is located close to the end of the first tube opposite that where the opening that receives air insufflation is located.

7. A probe according to claim 6, comprising a second conduit at the first tube wall, which extends along the length of the first tube, being connectable to an external means, and having, close to one of the second conduit's ends, bores that communicate the interior of the first tube with the interior of said second conduit.

8. A probe according to claim 7, wherein the external means is a suction means.

9. A probe according to claim 7, further comprising a third conduit at the first tube wall, which extends along the length of the first tube, being connectable to an external means, and having, close to one of the third conduit's ends, bores that communicate the interior of said third conduit with the external region of the first tube.

10. A probe according to claim 9, wherein each of said second and third conduits has another end that extends out of the first tube for coupling a first connection means, which has a switch for controlling suction at said second and third conduits and being coupled to a suction means.

11. A probe according to claim 10, wherein said first conduit, which links the interior of the first cuff to the interior of the first tube, is connectable to a second connection means, which has a switch for controlling an operation mode of said probe.

12. A probe according to any one of claims 1, and 8 to 4, comprising means that provide the first tube with an elastic memory, located along the wall of the first tube.

13. A probe according to claim 12, wherein said means that provide the first tube with an elastic memory are radiopaques.

* * * * *